United States Patent [19]
van de Veen

[11] Patent Number: 5,181,931
[45] Date of Patent: Jan. 26, 1993

[54] SWIVEL CONNECTION BETWEEN TWO PARTS OF AN ORTHOPEDIC TECHNICAL AID

[75] Inventor: Paul G. van de Veen, Enschede, Netherlands

[73] Assignee: Otto Bock Orthopaedische Industrie Besitz- und Verwaltungs-Kommanditgesellschaft, Duderstadt, Fed. Rep. of Germany

[21] Appl. No.: 647,027

[22] Filed: Jan. 28, 1991

[30] Foreign Application Priority Data

Jan. 26, 1990 [NL] Netherlands ............... 9000195
Feb. 19, 1990 [DE] Fed. Rep. of Germany ....... 4004988

[51] Int. Cl.$^5$ ............................ A61F 2/64; A61F 2/68
[52] U.S. Cl. ........................ 623/40; 623/42; 623/46
[58] Field of Search ............ 623/39, 44, 45, 46, 623/43, 42, 27, 32

[56] References Cited

U.S. PATENT DOCUMENTS 3,823,424  7/1974  May.
4,310,932  1/1982  Näder et al. ............... 623/45 X

FOREIGN PATENT DOCUMENTS

| 0306714 | 7/1918 | Fed. Rep. of Germany | ........ 623/27 |
| 414982 | 6/1925 | Fed. Rep. of Germany | . |
| 417623 | 8/1925 | Fed. Rep. of Germany | . |
| 448069 | 8/1927 | Fed. Rep. of Germany | . |
| 0200720 | 11/1958 | Fed. Rep. of Germany | ........ 623/39 |
| 1491233 | 5/1969 | Fed. Rep. of Germany | . |
| 2332993 | 1/1975 | Fed. Rep. of Germany | . |
| 0358545 | 1/1962 | Switzerland | ........................ 623/39 |
| 2194443 | 3/1988 | United Kingdom | . |

Primary Examiner—David Isabella
Assistant Examiner—Dinh X. Nguyen
Attorney, Agent, or Firm—Foley & Lardner

[57] ABSTRACT

The invention relates to a swivel connection between two parts of an orthopedic technical aid, for example a prosthesis or orthotic device, with an adjustable, inherent articulation stability, consisting of a plane kinematic articulation chain with at least four articulation members and a polycentric swiveling characteristic composed of translatory and rotatory components, the swiveling of at least one articulation member being limited in at least one swivel direction by a first swivel stop. For improving the function, it is proposed that at least one articulation member should be designed in such a way that its length can be altered under the action of an external force.

18 Claims, 9 Drawing Sheets

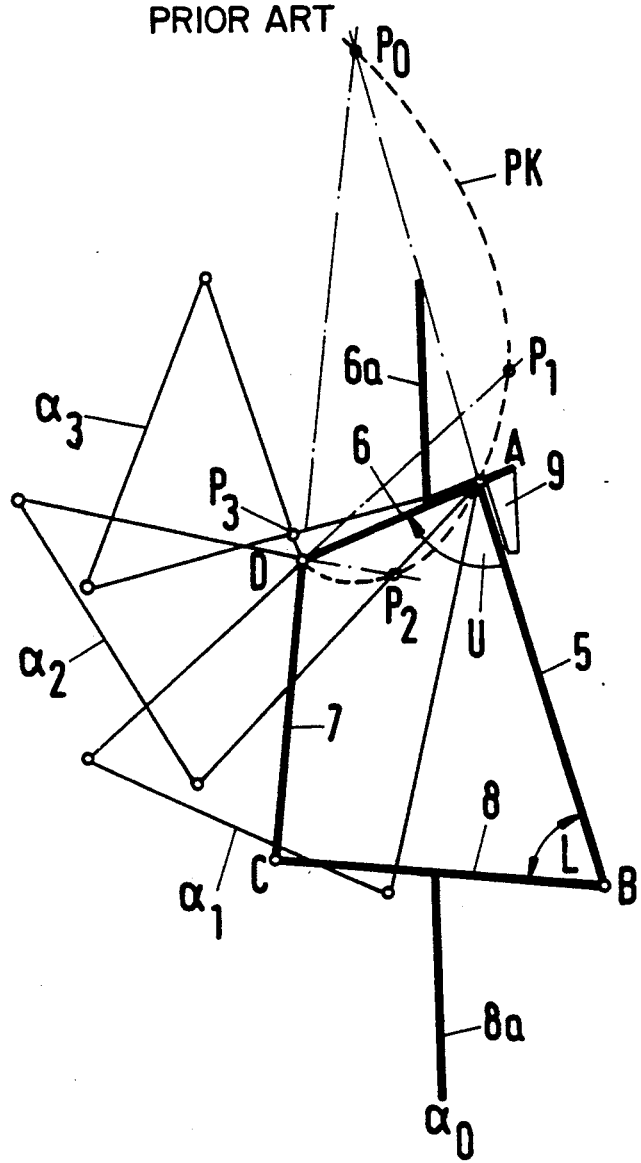

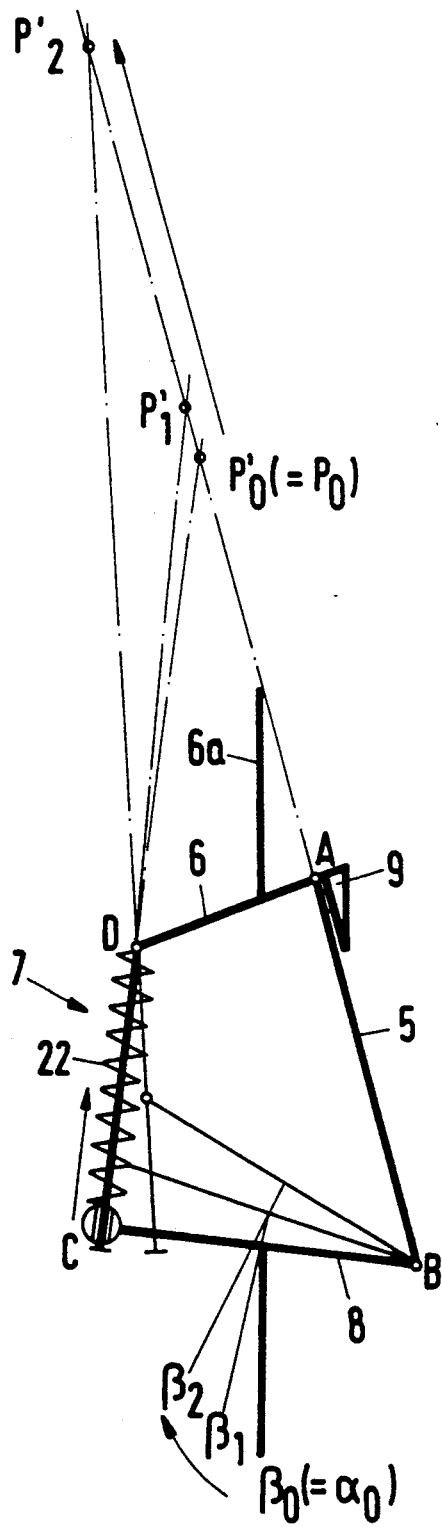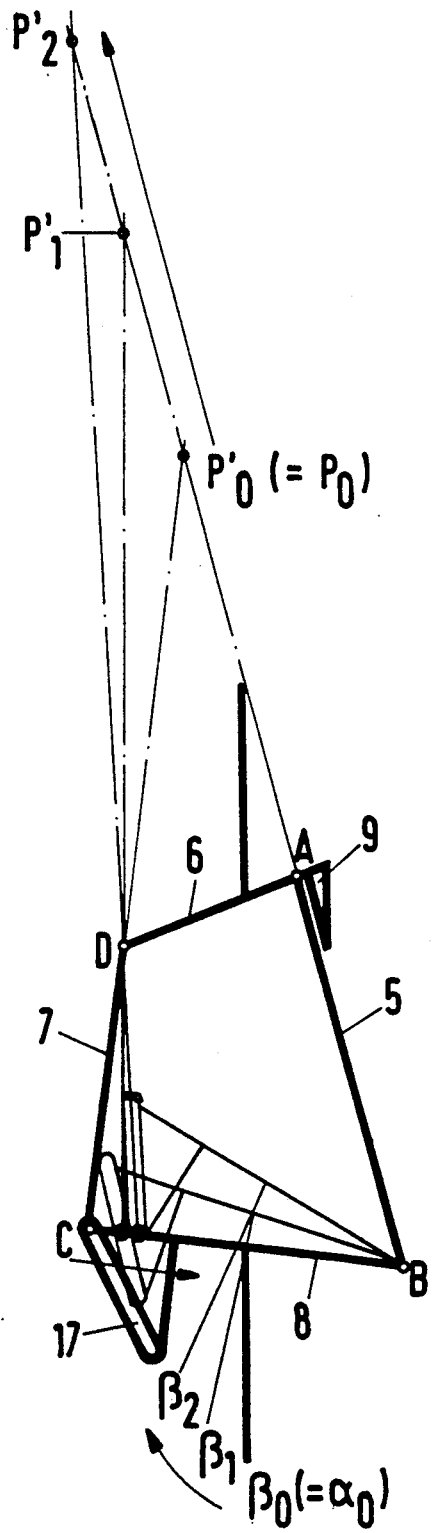

SWIVEL CONNECTION BETWEEN TWO PARTS OF AN ORTHOPEDIC TECHNICAL AID

BACKGROUND OF THE INVENTION

1. Field of the Invention

The present invention relates to a swivel connection between two parts of an orthopedic technical aid, and more specifically is directed to a swivel connection having an adjustable, inherent articulation stability.

2. Description of the Related Art

Swivel connections are used, for example, in knee-joint prosthesis. Their flexion properties are characterized by a polycentric movement composed of translatory and rotatory components, which movement corresponds to the rolling of two curves on one another, whose respective point of contact constitutes the momentary pivot of the movement. Each of these so-called pole curves is assigned to one of the parts of the prosthesis connected to one another by means of the polycentric swivel connection. Depending on the layout of their basic geometry, such polycentric knee-joints afford—in addition to advantages in the sitting position—particular advantages during the stationary phase of walking (calculated from heel contact until lifting-off of the point of the foot) compared to monocentric, i.e., single-axis, knee-joint designs.

A monocentric knee-joint prosthesis, which is statically secured during standing by exclusive rearward movement of the single axis position behind the load line, becomes, under heel load at the start of the stationary phase of walking, unstable on account of the altered load direction and must consequently be secured against buckling by the amputee initiating a hip extension moment. The degree of this moment is reduced by a more rearward displacement of the central axis. However, such an increased rearward displacement of the central axis substantially increases the hip moment required to flex the knee joint at the end of the stance phase of walking, i.e., the physical effort required by the wearer to initiate the first walking stride by flexing of the knee joint from a standstill position is substantially increased. Consequently, the physical effort on the part of the amputee can only be lessened by reducing the rearward movement of the central axis, which in turn requires, on account of the associated loss of stability, compensatory measures such as, for example, the integration of additional stationary phase securing elements in the form of mechanical brakes or hydraulic dampers.

In contrast, at a correspondingly high position of the momentary pivot of the extension position, a polycentric knee-joint prosthesis can have, not only during standing but also under heel load at the start of the stationary phase of walking, such a marked inherent stability that it is secure in the extended position without any hip extension moment. With a corresponding design, a further advantage can be obtained at the end of the stationary phase, at which point the natural walking pattern, for harmonic transition to the subsequent swing phase, provides for the initiation of a knee-bending under anterior foot load. This cannot be imitated by a prosthesis with a rearward-displaced, monocentric knee-joint, since the average amputee cannot apply the necessary hip flexion moment for an indefinite period of time. In contrast, the flexion of a prosthesis equipped with a polycentric knee-joint of the above-mentioned design under anterior foot load at the end of the stationary phase requires a far smaller hip flexion moment, which the average amputee can apply without tiring. However, these advantages can only be achieved if in each case the optimal position can be adjusted for the momentary pivot of the extension position.

Notwithstanding the advantages of a polycentric knee-joint prosthesis having the above-mentioned functional features, there is generally one disadvantage: its pronounced inherent stability in the extension position becomes lost at small flexion angles. It has therefore not been possible to design an artificial leg that affords an amputee the possibility of initiating, during an approximation of a natural walking pattern, an elastically spring-cushioned and/or damped knee flexion without loss of stability at the start of the stationary phase of walking under heel load in order to garner effective shock absorption while further improving the walking pattern and ergonomics in order to render the vertical movement of the body's center of gravity during the entire course of the stationary phase more balanced and more harmonic.

In the field of prosthetics, and in particular, orthopedics, the term below-knee prosthesis or "BK-Prosthesis" is used to indicate a type of prosthesis used for patients who have an amputation below the natural knee joint. The term through-knee prosthesis or "TK Prosthesis" is used to indicate a type of prosthesis used for patients who have an amputation just through or almost through the natural knee joint. The term above-knee prosthesis or "AK-Prosthesis" is used to indicate a type of prosthesis used for patients who have an amputation of the thigh, above the natural knee joint. The terms "hip-disarticulation prosthesis" or "hemi-pelvectomy prosthesis" is used to indicate prosthesis used for patients who have amputations just through, near or above the natural hip joint.

SUMMARY OF THE INVENTION

The present invention overcomes the problems and disadvantages of the prior art by providing a novel swivel connection between two parts of an orthopedic technical aid. The present invention represents a vast improvement and a completely novel approach for satisfying and meeting the needs, requirements and criteria for effective and useful swivel devices for orthopedic devices in a safe and cost effective manner.

The objects of the present invention are based on extending the function of a polycentric swivel connection.

Additional objects and advantages of the present invention will be set forth, in part, in the description which follows and, in part, will be obvious from the description or may be learned by practice of the invention. The objects and advantages of the invention may be learned by and attained by means of the instrumentalities and combination of steps particularly pointed out in the appending claims.

To achieve the foregoing objects and in accordance with the purpose of the present invention, as embodied and broadly described herein, the swivel connection of the present invention provided between two movable parts of an orthopedic device comprises a plane kinematic articulation chain having at least four articulation members and exhibiting a polycentric swiveling characteristic consisting of translatory and rotatory components, wherein the swiveling of at least one articulation member is limited in at least one swivel direction by a swivel stop and the length of at least one articulation member is capable of being altered by action of an external force.

According to the invention, this object is achieved by virtue of the fact that at least one articulation member is designed in such a way that its length can be altered under the action of an external force. This length alteration can be achieved, for example, by means of the fact that an articulation point connecting two articulation members to one another is displaceable under load in the direction of the one and/or the other articulation member.

In some cases a resistance device counteracting said length alteration is provided, which device can be, for example, a device generating mechanical friction, a damper or the like.

Particular advantages can be obtained if the length alteration of at least the one articulation member is designed in a spring-elastic manner. In this design the length alteration in each case takes place counter to the action of a restoring force. Springs, rubber-elastic or pneumatic devices or the like can be provided for this purpose. It is also possible in principle to design the length-variable articulation member as a leaf spring.

In an illustrative layout of the construction according to the invention, the load-dependent shortening of the space between two neighboring articulation points results in a load-dependent flexor-side swiveling of the lower part of the articulation relative to the upper part of the articulation, with simultaneous movement of the momentary pivot away from the swivel connection in a straight line which is inclined with respect to its flexor side and which is in alignment with the longitudinal axis of the articulation member whose limit position preset by the swivel stop is maintained.

This load-dependent additional kinematic leads to an increase in the adjustable inherent articulation stability, the construction according to the invention making it possible to influence the adjustable inherent articulation stability in other ways by simple variations in mechanism technology: the swivel connection according to the invention is generally characterized by the ability to permit a limitable and controllable additional movement in a preset direction under the action of an external load and thereby at the same time influence qualitatively and quantitatively the adjustable inherent articulation stability in a specific manner depending on the constructional design, either in the sense of an exclusive reduction, maintenance or increase of these effects or in the sense of an additional movement-dependent combination of these effects.

Thus, where reference is made in the following description to a knee-joint, this is merely an illustrative, albeit particularly advantageous, application of the swivel connection according to the invention.

When used as a knee-joint, the swivel connection according to the present invention affords the possibility of a knee flexion under heel load at the start of the stationary phase of walking, without any restriction on the advantages described above in conjunction with the previously known polycentric knee-joint prosthesis. A knee-joint prosthesis designed according to the present invention is therefore significantly superior in terms of function to the monocentric designs which have become known as "bouncing knees".

For setting the articulation stability, it is advantageous if the first swivel stop is adjustable. The greatest possible freedom for setting the articulation stability can, however, only be achieved if additional measures are provided, for example, a manual length alteration of an articulation member.

The improved stability of the loaded swivel connection is particularly significant, especially when used as a knee-joint, if the first swivel stop is arranged between two rigidly designed articulation members, one of these two articulation members preferably being formed by the upper connection part.

When the swivel connection according to the invention is used as a knee-joint, a first part of the orthopedic technical aid constitutes an upper part of a prosthesis for an amputee with an amputation through or above the knee, a second part constitutes a lower part of a prosthesis for an amputee with an amputation through or above the knee, and a four-membered articulation chain constitutes a knee-joint. For ease of reference, the first part of the orthopedic technical aid that constitutes an upper part of a prosthesis for an amputee with an amputation through or above the knee will be referred to as a thigh prosthesis, and the second part that constitutes a lower part of a prosthesis for an amputee with an amputation through or above the knee will be referred to as a lower leg prosthesis. Referring to the four-membered articulation chain, two articulation members are connected securely to the thigh prosthesis and lower leg prosthesis, respectively, and are joined to one another by a front articulation member (extensor-side coupling member) used for setting the extension position and b a rear articulation member (flexor-side coupling member) at articulation points. According to the invention, the flexor-side coupling member is then preferably the articulation member whose length can be altered in spring-elastic manner under load.

It is additionally expedient if the articulation point connecting the flexor-side coupling member to the lower articulation member is arranged longitudinally displaceable within the lower articulation member and can be fixed in the desired position.

Further features of the invention form the subject-matter of the subclaims and are explained in greater detail, in conjunction with further advantages of the invention, on the basis of exemplary embodiments.

The accompanying drawings, which are incorporated in and constitute a part of this specification, illustrate one embodiment of the present invention and, together with the description, serve to explain the principles of the present invention.

BRIEF DESCRIPTION OF THE DRAWINGS

FIG. 1 is a schematic diagram of a polycentric articulation according to the prior art, shown in the extended position;

FIG. 2 is a schematic diagram of a polycentric swivel connection according to the present invention, shown in the extended position;

FIG. 3 is a schematic diagram of another modified embodiment of the polycentric swivel connection of the present invention, shown in the extended position;

DESCRIPTION OF THE PREFERRED EMBODIMENTS

Figure 4:
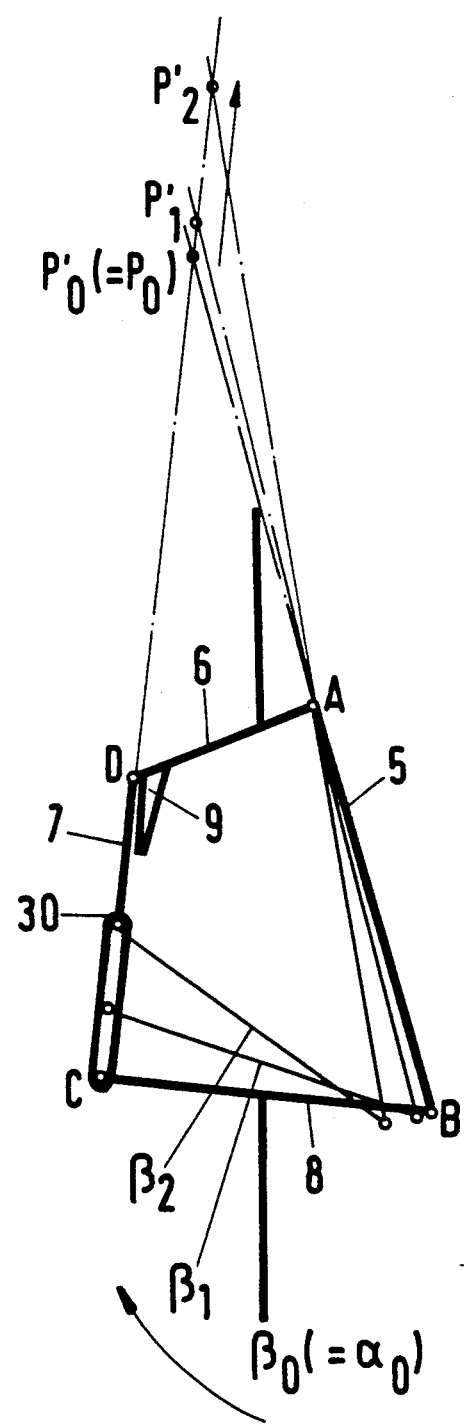
FIG. 4 is a schematic diagram of a modified embodiment of the polycentric swivel connection of the present invention, shown in the extended position.

Reference will now be made, in detail, to preferred embodiments of the present invention, examples of which are illustrated in the accompanying drawings and are represented generally by the reference numeral 1. Whenever possible, the same reference numbers will be used throughout the drawings to refer to the same or like parts.

FIG. 1 shows diagrammatically a swivel connection in the extended position, consisting of a plane kinematic articulation chain with four articulation members 5, 6, 7, 8, which are joined to one another at four articulation points A, B, C, D. The upper articulation member 6 can be connected to the upper part of an orthopedic technical aid by means of a diagrammatically represented attachment device 6a. In the same way, the lower articulation member 8 has an attachment device 8a for the lower part of an orthopedic technical aid. The articulation member 5 on the right in FIG. 1 is an extensor-side coupling member, opposite which there is a flexor-side coupling member formed by the articulation member 7 shown on the left. The extension position of this swivel connection is defined by a stop 9 which, in the embodiment shown, limits the maximum extent of the angle U included between the upper articulation member 6 and the extensor-side coupling member 5. This is a previously known swivel connection in which the distances between the neighboring articulation points are in each case unalterable.

The flexion characteristics is represented, starting from the extended position ($\alpha_1$, $\alpha_2$, $\alpha_3$) of the lower part of the articulation relative to the stationary upper part of the articulation. This flexion characteristic is composed of a translatory and a rotatory component and leads to a polycentric movement which is described by the broken-line pole curve PK (fixed polode) pertaining to the stationary upper part of the articulation, which pole curve connects to each other all the momentary pivots P pertaining to the respective flexion positions, of which pivots, in the example illustrated, the momentary pivot $P_0$ pertaining to the extension position lies furthest above the articulation.

FIG. 2 shows a swivel connection according to the present invention. In contrast to the embodiment according to FIG. 1, the flexor-side coupling member 7 of the present invention is designed in such a way that its length can be altered in a spring-elastic manner under the action of an external pressure force (not shown in detail in the drawing), by its lower articulation point C being displaceable in the direction of its upper articulation point D counter to the action of a compression spring 22. Starting from the initial no-load position ($\beta_0=\alpha a_0$), two load-dependent displacement positions of the articulation point C are shown, which lead to a swiveling of the lower articulation member 8 by the angle $\beta_1$ or $\beta_2$ and to a swiveling of the flexor-side coupling member 7 about its upper articulation point D. Compared to the representation according to FIG. 1, FIG. 2 concerns load-dependent additional kinematics which are identified in the drawings in each case by the angle $\beta$ and which are recognizable by the fact that the angular position, preset by the stop 9, between the rigidly designed articulation members 5, 6 is maintained.

The load-dependent additional kinematics in turn effect a flexion movement of the lower part of the swivel connection relative to the stationary upper part, with simultaneous displacement of the momentary pivot P, which in each case is defined by the point of intersection of the extension lines of both coupling members 5, 7. In this case, the displacement of the momentary pivots P takes place as a function of the flexion position $\beta$ of the lower part along a straight line representing the extension of the longitudinal axis of that coupling member 5, 7 whose limit position preset by the stop 9 is maintained. Thus, in the exemplary embodiment according to FIG. 2, all the momentary pivots $P'_0$, $P'_1$ and $P'_2$ lie on the extension (shown by a dot-and dash line) of the coupling member 5, the momentary pivots $P'$ in the chosen example becoming further removed from the articulation as the flexion angle $\beta$ increases. This effect of the solution according to the invention is of the greatest importance.

The exemplary embodiment according to FIG. 3 differs from that according to FIG. 2 only in that the articulation point C is not displaceable under load in the direction of articulation point D, but in the direction of articulation point B counter to the action of a spring or the like (not shown). In this case, articulation point C is displaced within a longitudinal slot 17 in such a way as to result in a load-dependent swiveling of the lower articulation member 8 and a displacement of the momentary pivot P analogously to FIG. 2.

FIG. 4 shows an embodiment comparable to that in FIG. 2, the only difference being that the stop 9 now limits the swiveling of the flexor-side coupling member 7 relative to the upper articulation member 6. The displacement of the momentary pivots $P'$ as a function of the flexion position $\beta$ of the lower part of the swivel connection relative to the stationary upper part thus takes place along the extension (shown by a dot-and-dash line) of the flexor-side coupling member 7. Moreover, a length stop 30 is indicated, which limits the maximum extent of the spring-elastic shortening of the flexor-side coupling member 7 or displacement of articulation point C relative to articulation point D.

Figure 5:
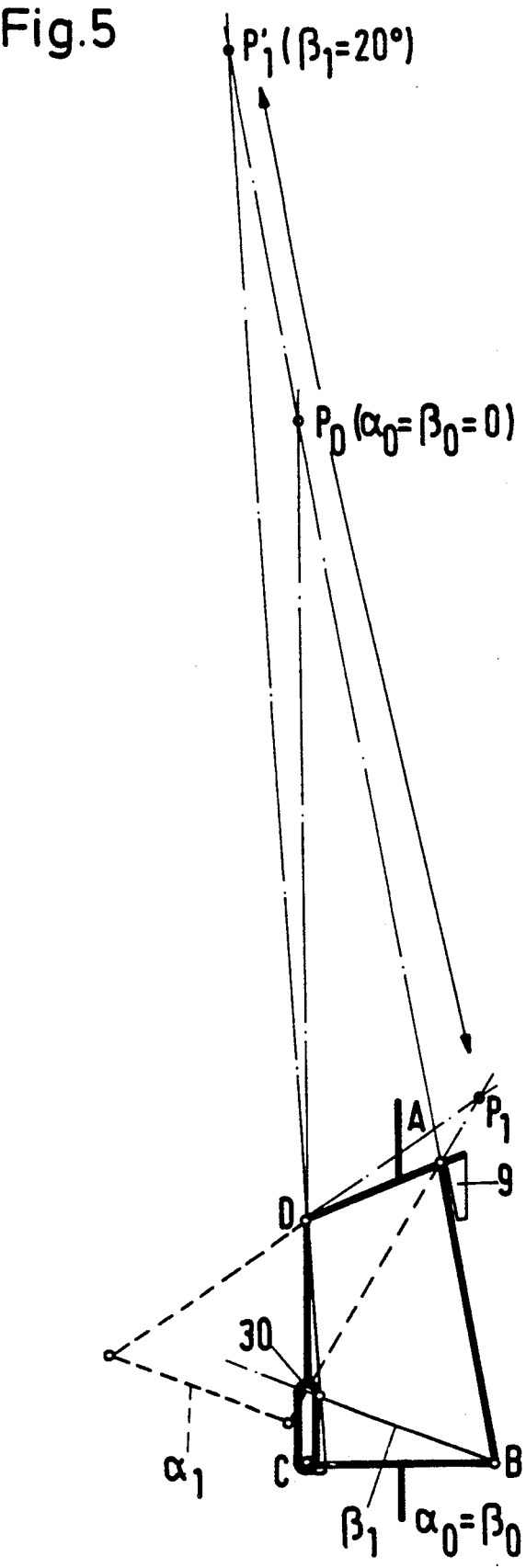
FIG. 5 is a comparative schematic diagram of the polycentric swivel connection of the present invention under the effects of load-independent basic kinematics and load-dependent additional kinematics.
Figure 6:
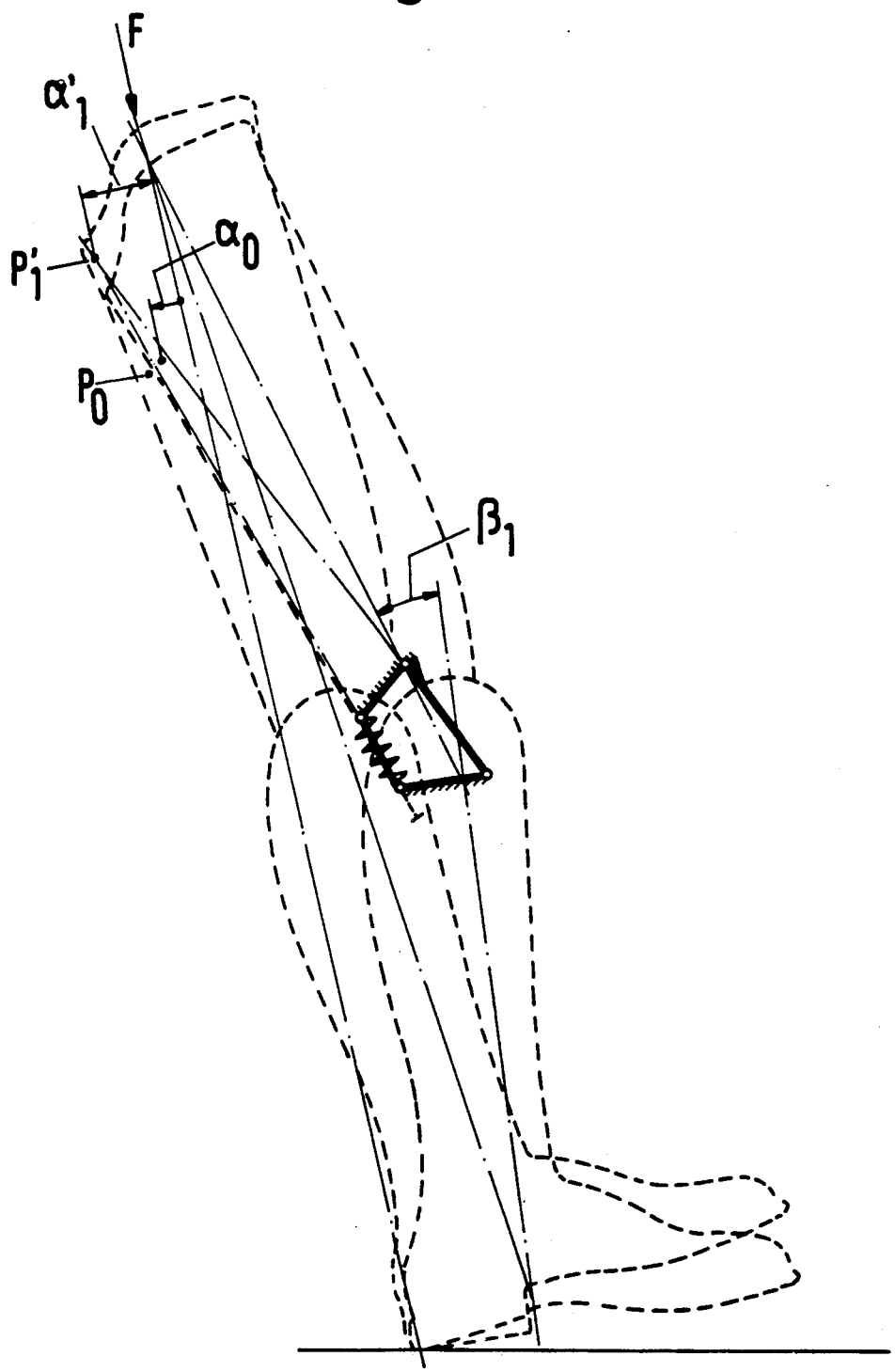
FIG. 6 shows the embodiment according to FIG. 5 as a knee-joint prosthesis.

FIG. 5 shows a swivel connection according to the present invention and makes clear the significant advantage of the load-dependent additional kinematics, obtained according to the invention, compared to the conventional load—independent basic kinematics. Whereas, when using basic kinematics at a flexion angle $\alpha_1=20°$, the momentary pivot $P_1$ lies closely above the articulation and in front of its extensor-side limit, at a load-dependent flexion angle $\beta_1=20°$ a momentary pivot $P'_1$ is obtained, which lies far above the articulation and behind its flexor-side limit. This is even clearer in FIG. 6, in which the basic geometry of the swivel connection according to FIG. 5 has been taken over true to scale. The knee extension moment $M_0=F\times d_0$ generated in the extension position under the action of the load F directed to the heel increases in the case of a knee flexion using the load-dependent additional kinematics, to more than twice the value $M'_1=F\times d'_1$. In the case of a knee flexion merely using the load-independent basic kinematics of a conventional construction, there would in contrast be an extremely high, inversely directed flexion moment, which could no longer be compensated muscularly and which would thus inevitably lead in practice to the amputee stumbling or falling.

FIGS. 7 to 10 show a particular exemplary embodiment for using the swivel connection according to the invention in a knee-joint prosthesis.

Figure 7:
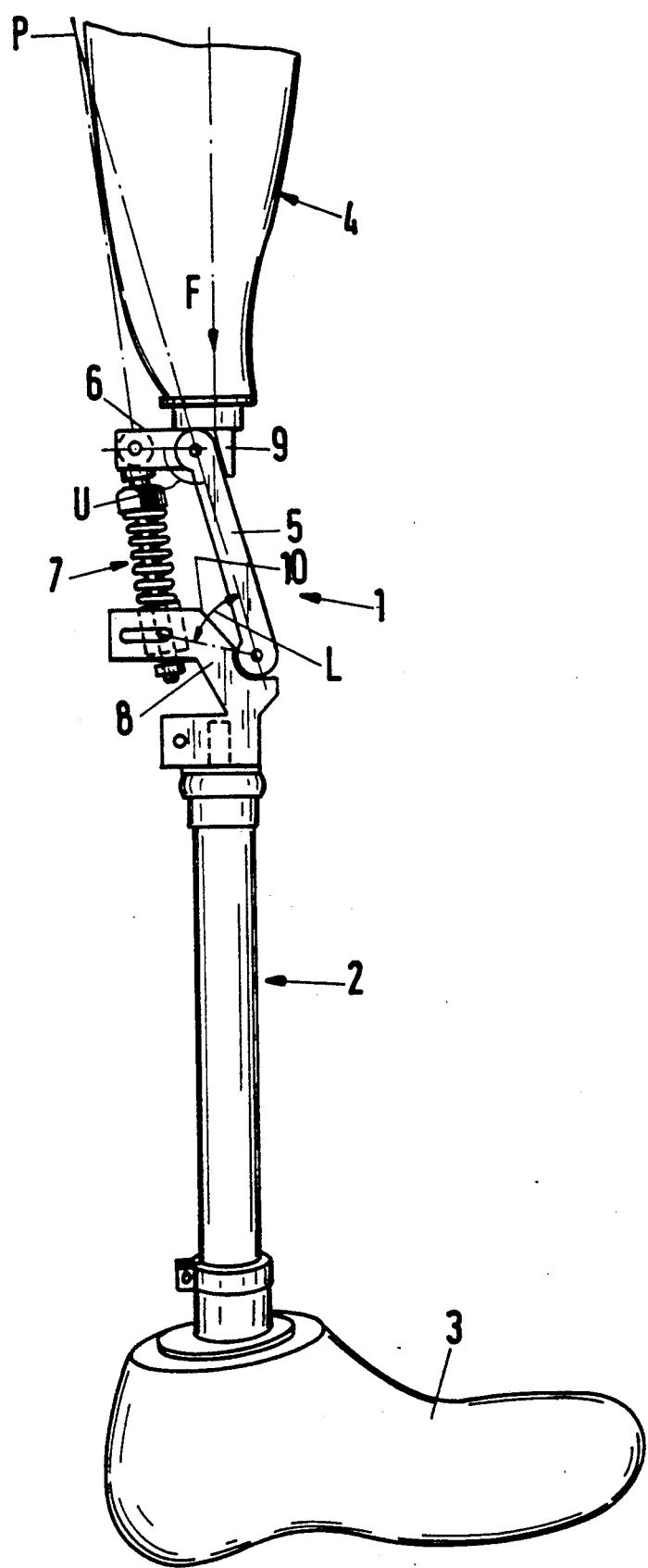
FIG. 7 shows a perspective representation of an artificial leg with a knee-joint prosthesis according to FIG. 6.

The knee-joint 1 connects a lower leg prosthesis 2 to a thigh prosthesis 4. The knee-joint 1 is essentially formed by a plane kinematic articulation chain consisting of four articulation members 5, 6, 7, 8. The upper articulation member 6 is connected securely to the upper prosthesis part 4, and the lower articulation member 8 is connected securely to the lower prosthesis part 2. The articulation member 7 shown on the left in the drawing is designed as a flexor-side coupling member which can be shortened under load. The momentary pivot P of the lower prosthesis part 2 relative to the upper prosthesis part 4 arises from the point of intersection of the extensions (shown in dot-and-dash lines) of both coupling members 5, 7. A first swivel stop 9 limits the swiveling of the coupling member 5 relative to the upper articulation member 6 and thereby defines the outermost extension position of the knee-joint 1, which additionally has a second swivel stop 10 which defines the smallest angle between the articulation members 5, 8 and thereby limits the shortening of the coupling member 7. In FIG. 7, the angle defined between the extensor-side coupling member 5 and the upper articulation member 6 is designated by U, and the angle included between the extensor-side coupling member 5 and the lower articulation member 8 is designated by L.

The prosthesis shown in FIGS. 7 to 10 is constructed in detail as follows:

The lower leg prosthesis 2 is made up of a modular part at whose lower end a foot prosthesis 3 is secured. The upper prosthesis part 4 can be designed for connection to a thigh stump or a knee articulation stump.

Figure 8:
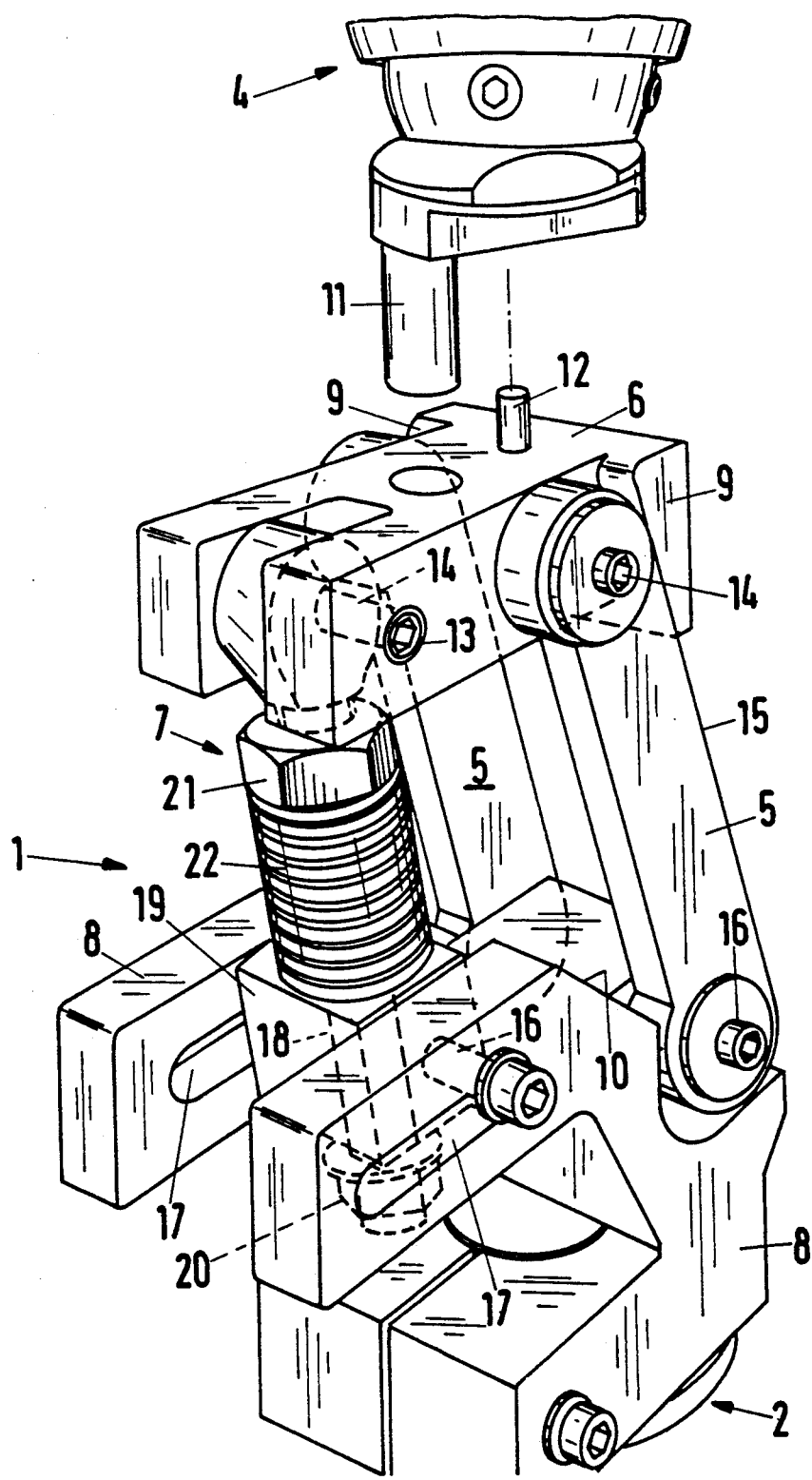
FIG. 8 shows a perspective representation, and partly exploded representation of a detail of the knee-joint according to FIG. 7.
Figure 9:
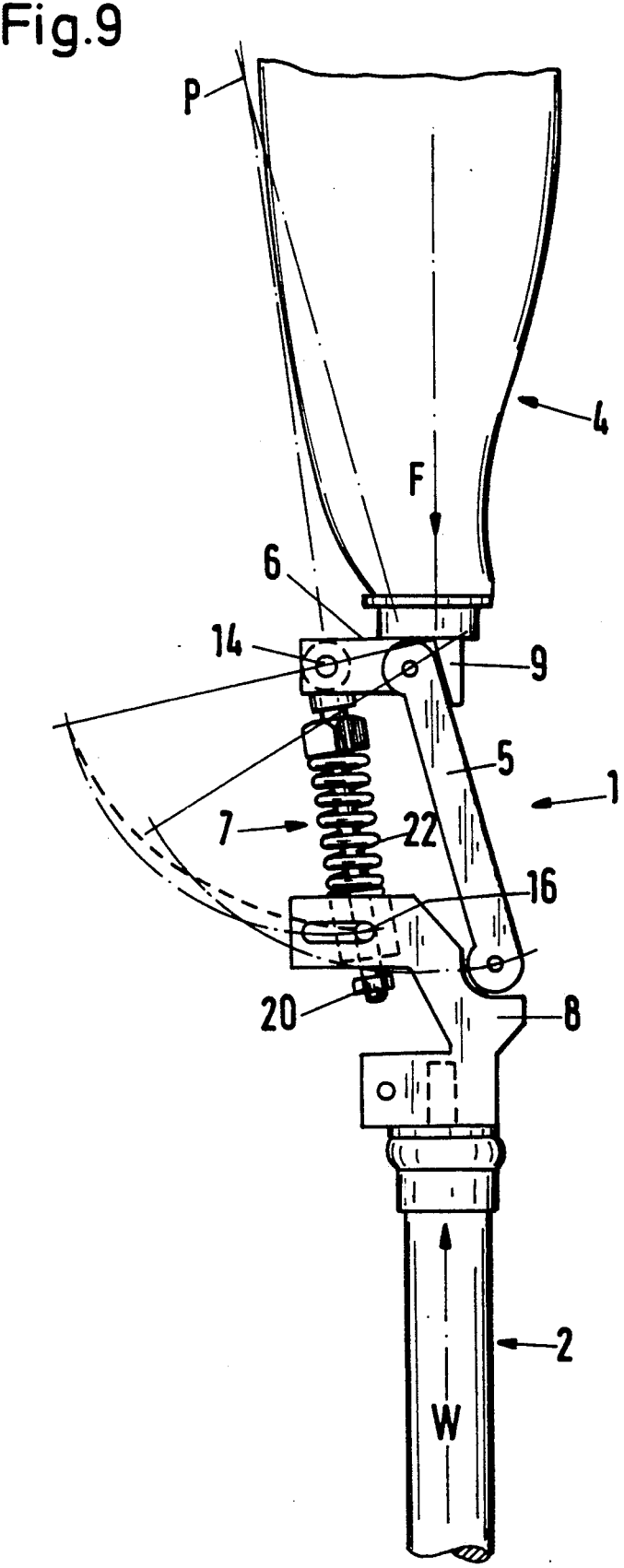
FIG. 9 shows, on an enlarged scale, a side view of the detail in FIG. 7 with the swivel range indicated.

The upper articulation member 6 is secured, fixed in terms of rotation, to a coupling part of the upper prosthesis part 4 by means of a bolt il and pin 12 (see in particular FIG. 8). The upper end of each coupling member 5, 7 is in each case articulated in swivel fashion on the upper articulation member 6 via swivel devices 14 arranged in bores 13 of the upper articulation member 6. The first swivel stop 9 is arranged securely on the upper articulation member 6, cooperates with the front surface 15 of the extensor-side coupling member 5 (FIG. 8) and limits the swiveling angle U thereof (see FIG. 7). This first swivel stop 9 can be of adjustable design, although this is not shown in the drawing, so that the basic geometry of the four-membered articulation chain and the location of its momentary pivot in the extension position can be altered, in order to be able to adapt the basic setting of the prosthesis to the individual requirements of the amputee in terms of safety and dynamics.

The lower end of each coupling member 5, 7 is articulated in each case via a swivel device 16 on the lower articulation member 8, which is secured by clamping on the upper end of the modular part 2. The swivel device 16 articulating the lower end of the flexor-side coupling member 7 is guided through longitudinal slots 17 in the lower articulation member 8 and can be fixed in the desired position within the longitudinal slots 17. In this way the position of the flexor-side coupling member 7 relative to the extensor-side coupling member 5 can be varied by manually altering the length of the lower articulation member 8, in order to optimize in particular the height position of the momentary pivot P and, thus, the overall stability of the knee joint 1.

The flexor-side coupling member 7 comprises a bolt 18 whose lower end is guided longitudinally displaceably in a support body 19 mounted so as to swivel on the swivel device 16. A nut 20 is screwed on the lower end of the bolt 18, which nut, in the unloaded state of the swivel movement, determines the effective basic length of the coupling member 7, which can be of adjustable design - for example by using a further (counter) nut—in order to obtain an additional adjusting possibility.

A nut 21 is also screwed onto the upper end of the bolt 18, which nut can be adjusted relative to the bolt eye articulating on the upper swivel device 14 and forms an abutment for a compression spring 22 whose lower end bears on the support body 19. The prestress or tension of the compression spring 22 can be adjusted by turning the upper nut 21.

When the knee joint 1 is loaded, for example by the body weight of the prosthesis user, the compression spring 22 is compressed, with simultaneous displacement of the bolt 18 relative to the support body 19. In this way the distance between the two swivel devices 14, 16 and, thus, the effective length of the flexor-side coupling member 7 important for the kinematics of the articulation are reduced. As a consequence of this, the position of the momentary pivot is altered.

However, the flexor-side coupling member 7 could also be designed, for example, as a leaf spring which bends more under load, as a result of which the distance of the two swivel points 14, 16 from one another would likewise be reduced.

When the prosthesis is in the extended state (FIG. 9) and is loaded in this position, for example, by the weight F of the prosthesis user, it is of great importance that the momentary pivot P should lie behind the load line, since only in this way is it possible to prevent the multi-membered articulation chain from executing a swivel corresponding to its basic kinematics under the effect of the load. Since, in the extended state, the position of the articulation members 5, 6 relative to one another is predetermined by the first swivel stop 9, the shortening of the effective length of the articulation member 7 results in a displacement of the momentary pivot P in a line arising from an extension of the front articulation member 5 or the connection line between its two articulation points 14, 16. In order to achieve the greatest possible stability, it is important that this line should always lie behind the line of application of the load F.

Figure 10:
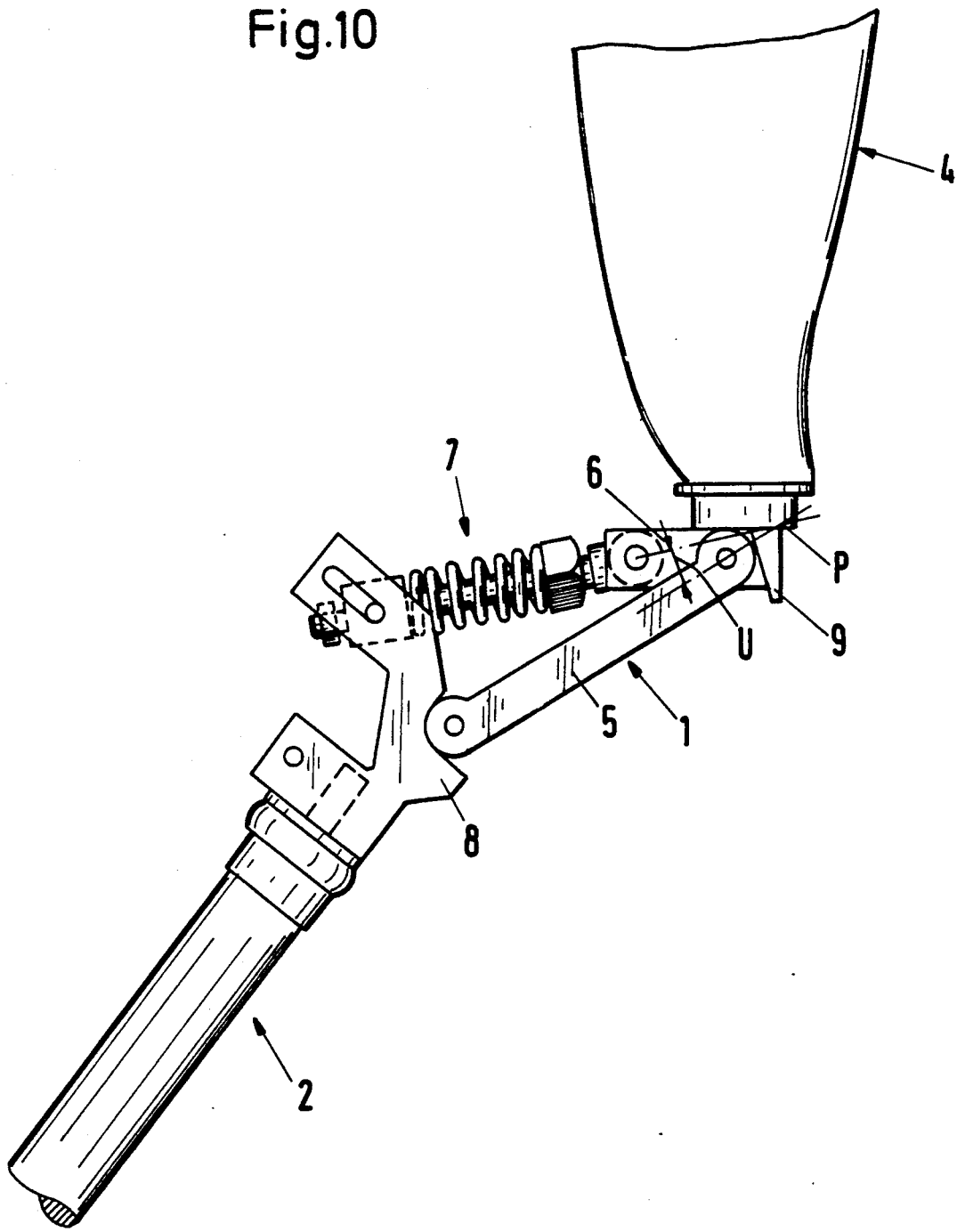
FIG. 10 shows the representation according to FIG. 9 in the flexion position.

For the purposes of comfort in using an artificial leg with a polycentric knee-joint it is of great importance that, as the knee flexion angle increases—as is particularly the case during the swing phase or in the sitting position the momentary pivot P should move into a position near the knee, as can be seen in FIG. 10.

It will be apparent to those skilled in the art that various modifications and variations can be made in the method and apparatus of the present invention without departing from the scope or spirit of the invention. It is intended that the present invention cover such modifications and variations of this invention provided they come within the scope of the appended claims and their equivalents.

What is claimed is:

1. A swivel connection provided between two movable parts of an orthopedic device comprising at least four articulation members forming a plane kinematic articulation chain and exhibiting a polycentric swiveling characteristic consisting of translatory and rotatory components, wherein a swiveling movement of at least one articulation member is limited in at least one swivel direction by a swivel stop and the length of at least one articulation member is variable by action of an external force.

2. The swivel connection as claimed in claim 1, wherein an articulation point connecting two articulation members to one another is displaceable under load in the direction of the one and/or the other articulation member.

3. The swivel connection as claimed in claim further comprising a resistance device counteracting said length alteration.

4. The swivel connection as claimed in claim 1, wherein the length alteration of at least the one articulation member is designed in a spring-elastic manner.

5. The swivel connection as claimed in claim wherein the swivel stop is adjustable.

6. The swivel connection as claimed in claim 1, wherein the swivel stop is arranged between two rigidly designed articulation members.

7. The swivel connection as claimed in claim wherein the maximum extent of the shortening of the articulation member or of the displacement of the articulation point is limited by a length stop.

8. The swivel connection as claimed in claim 1, wherein the maximum extent of the shortening of the articulation member or of the displacement of the articulation point is limited by a second swivel stop.

9. The swivel connection as claimed in claim 7, wherein the length stop is adjustable.

10. The swivel connection as claimed in claim 8, wherein the second swivel stop is adjustable.

11. The swivel connection as claimed in claim 1, in which a first part of the orthopedic technical aid constitutes a thigh prosthesis, a second part constitutes a lower leg prosthesis, and a four-membered articulation chain constitutes a knee joint, whose two articulation members connected securely to the thigh prosthesis and lower leg prosthesis, respectively, are connected to one another by a third, extensor-side coupling, articulation member used for setting the extension position and by a fourth, flexor-side couplings articulation member at articulation points, wherein the length of said fourth, flexor-side coupling, articulation member is variable in a spring-elastic manner under load.

12. The swivel connection as claimed in claim 11, wherein the swivel stop acts on the third, extensor-side coupling, articulation member and limits the maximum extent of the angle included between the upper articulation member and the third, extensor-side coupling, articulation member.

13. The swivel connection as claimed in claim 11, wherein the fourth, flexor-side coupling, articulation member is supported at an articulation point on a lower articulation member by a compression spring.

14. The swivel connection as claimed in claim 13, wherein the compression spring has a prestress that is adjustable.

15. A swivel connection provided between two movable parts of an orthopedic device comprising a plane kinematic articulation chain having at least four articulation members and exhibiting a polycentric swiveling characteristic consisting of translatory and rotatory components, wherein a swiveling movement of at least one articulation member is limited in at least one swivel direction by a swivel stop and the length of at least one articulation member is variable by action of an external force, wherein a first part of the orthopedic technical aid constitutes a thigh prosthesis, a second part constitutes a lower leg prosthesis, and a four-membered articulation chain constitutes a knee joint, whose two articulation members connected securely to the thigh prosthesis and lower leg prosthesis, respectively, are connected to one another by a third, extensor-side coupling, articulation member used for setting the extension position and by a fourth, flexor-side couplings articulation member at articulation points, wherein the length of said fourth, flexor-side coupling, articulation member is variable in a spring-elastic manner under load, and wherein the articulation point connecting the fourth, flexor-side coupling, articulation member to a lower articulation member is arranged longitudinally displaceable within the lower articulation member and can be fixed in a desired position.

16. The swivel connection as claimed in claim 15, wherein said longitudinal displaceability extends over a circular arc section with the upper articulation point as mid-point.

17. The swivel connection as claimed in claim 16, wherein, with the articulation extended, the length alteration of the articulation member and the longitudinal displacement of the articulation point take place approximately in the direction of and parallel to a load vector.

18. The swivel connection as claimed in claim 13, wherein the fourth, flexor-side coupling, articulation member effective in the unloaded state of the swivel connection has an adjustable length.

* * * * *